(12) United States Patent
Weber

(10) Patent No.: US 6,793,650 B2
(45) Date of Patent: Sep. 21, 2004

(54) DISPOSABLE TRAINING PANT DESIGNED SPECIFICALLY FOR LATE STAGE TOILET TRAINING

(75) Inventor: Shirlee Ann Weber, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 293 days.

(21) Appl. No.: 10/017,762

(22) Filed: Dec. 14, 2001

(65) Prior Publication Data

US 2003/0114810 A1 Jun. 19, 2003

(51) Int. Cl.⁷ ................................................. A61F 13/15
(52) U.S. Cl. ............... 604/396; 604/396; 604/385.101; 604/378; 604/385.16; 604/385.22
(58) Field of Search .................. 604/396, 385.101, 604/378, 385.16, 385.22

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,205,679 A | 6/1980 | Repke et al. | |
| 4,340,563 A | 7/1982 | Appel et al. | |
| 4,597,761 A | 7/1986 | Buell | |
| 4,641,381 A | 2/1987 | Heran et al. | |
| 4,655,760 A | 4/1987 | Morman et al. | |
| 4,663,220 A | 5/1987 | Wisneski et al. | |
| 4,701,171 A | 10/1987 | Boland et al. | |
| 4,701,175 A | 10/1987 | Boland et al. | |
| 4,704,114 A | 11/1987 | Wilson et al. | |
| 4,704,116 A | 11/1987 | Enloe | |
| 4,747,846 A | 5/1988 | Boland et al. | |
| 4,756,709 A | 7/1988 | Stevens | |
| 4,770,656 A | 9/1988 | Proxmire et al. | |
| 4,808,176 A | 2/1989 | Kielpikowski | |
| 4,847,134 A | 7/1989 | Fahrenkrug et al. | |
| 4,892,598 A | 1/1990 | Stevens et al. | |
| 4,936,840 A | 6/1990 | Proxmire | |
| 4,940,464 A | 7/1990 | Van Gompel et al. | |
| 5,046,272 A | 9/1991 | Vogt et al. | |
| 5,087,253 A | * 2/1992 | Cooper .................. 604/385.15 |
| 5,104,116 A | 4/1992 | Pohjola | |
| 5,224,405 A | 7/1993 | Pohjola | |
| 5,226,992 A | 7/1993 | Morman | |
| 5,261,899 A | * 11/1993 | Visscher et al. ............ 604/367 |
| 5,669,894 A | 9/1997 | Goldman et al. | |
| 5,947,947 A | * 9/1999 | Tanzer et al. ......... 604/385.101 |
| 6,140,551 A | * 10/2000 | Niemeyer et al. .......... 604/367 |
| 6,168,585 B1 | 1/2001 | Cesco-Cancian | |
| 6,174,303 B1 | 1/2001 | Suprise et al. | |
| 6,287,287 B1 | * 9/2001 | Elsberg ................. 604/385.03 |
| 6,506,959 B2 | 1/2003 | Hamajima et al. | |

FOREIGN PATENT DOCUMENTS

| | | |
|---|---|---|
| EP | 0 217 032 | 2/1992 |
| GB | 2 284 741 | 6/1995 |
| WO | 97/09013 | 3/1997 |
| WO | 99/25290 | 5/1999 |
| WO | 01/49230 | 7/2001 |

* cited by examiner

Primary Examiner—John J. Calvert
Assistant Examiner—Jacqueline F Stephens
(74) Attorney, Agent, or Firm—Pauley Petersen & Erickson

(57) ABSTRACT

A pant-like absorbent garment having an absorbent pad attached to a front region and a back region of an outer cover, wherein the absorbent pad is at least partially suspended therebetween to provide a close or customized fit for the wearer. The pant-like absorbent garment is suitable as a low capacity training pant for late stage toilet training.

37 Claims, 4 Drawing Sheets

DISPOSABLE TRAINING PANT DESIGNED SPECIFICALLY FOR LATE STAGE TOILET TRAINING

BACKGROUND OF THE INVENTION

This invention is directed to a low capacity disposable training pant for late stage toilet training having an absorbent pad suspended from a front and back waist region of an absorbent chassis to provide a close or customized fit against the wearer's body.

Toilet training a child is often not an easy task and thus training aids are commonly employed to help in training. However, many parents have found that conventional training pants, as well as conventional diapers, are unsuccessful in motivating their child to become toilet trained.

Some conventional highly absorbent training pants and diapers generally are so effective in absorbing insults, for example urine, that the child does not know when he or she is wearing a wet garment. This can confuse a child and possibly delay toilet training. Many parents believe that a wet sensation or a change in feeling experienced by the child during or after urination will discourage the child from wetting his or her garment and will help him or her complete toilet training.

Further, some conventional garments, for example training pants, closely resemble conventional diapers. Many parents believe that if a child cannot distinguish a training pant from a conventional diaper, he or she will not be motivated to keep his or her training pant dry.

There is a need or desire for a toilet training garment that motivates a child to complete the toilet training process.

There is a need or desire for a toilet training garment that provides a close or customized fit to the wearer's body to properly contain and absorb an insult.

There is a need or desire for a single insult disposable training pant usable as a toilet training aid which is capable of absorbing and containing one insult.

SUMMARY OF THE INVENTION

The present invention is directed to pant-like disposable absorbent garments or articles, for example single insult training pants, having an overall absorbent capacity of less than about 300 grams, suitably about 60 grams to about 200 grams, desirably about 100 grams to about 150 grams. Thus, the article is suitable as a late stage toilet training aid.

The pant-like disposable absorbent article includes an absorbent pad operatively joined to an absorbent chassis of the absorbent article. For example, in one embodiment of this invention, the absorbent pad can be joined to an outer cover and/or bodyside liner at a front waist region and/or a back waist region of the absorbent chassis, whereby the absorbent pad can be at least partially suspended therebetween. Desirably, the absorbent pad is made of a relatively thin, high swelling absorbent material such as an extremely thin, absorbent composite material or an ultra-thin-absorbent (UTA) material including a mixture of superabsorbent material and pulp fiber.

A stretchable pad attachment may join or attach the absorbent pad to the front waist region and the back waist region using suitable connecting or attaching means, for example intermittent ultrasonic bonds. Because the absorbent attachment is stretchable, the suspended absorbent pad can conform to the wearer's body to provide a custom or close fit. In one embodiment of this invention, the absorbent pad may also be connected to the outer cover and/or the bodyside liner at a crotch region of the absorbent chassis. Desirably, the absorbent article has a generally cloth-like texture and appearance and may have a refastenable side seam mechanism for easy donning and removal.

With the foregoing in mind, it is a feature and advantage of the invention to provide a pant-like absorbent garment having an absorbent pad which is suspended from an outer cover at a front waist region and a back waist region to provide a close or customized fit against the wearer's body.

It is further a feature and advantage of the invention to provide a low capacity pant-like absorbent garment, such as a training pant, which is suitable for late stage toilet training.

DEFINITIONS

Figure 1:
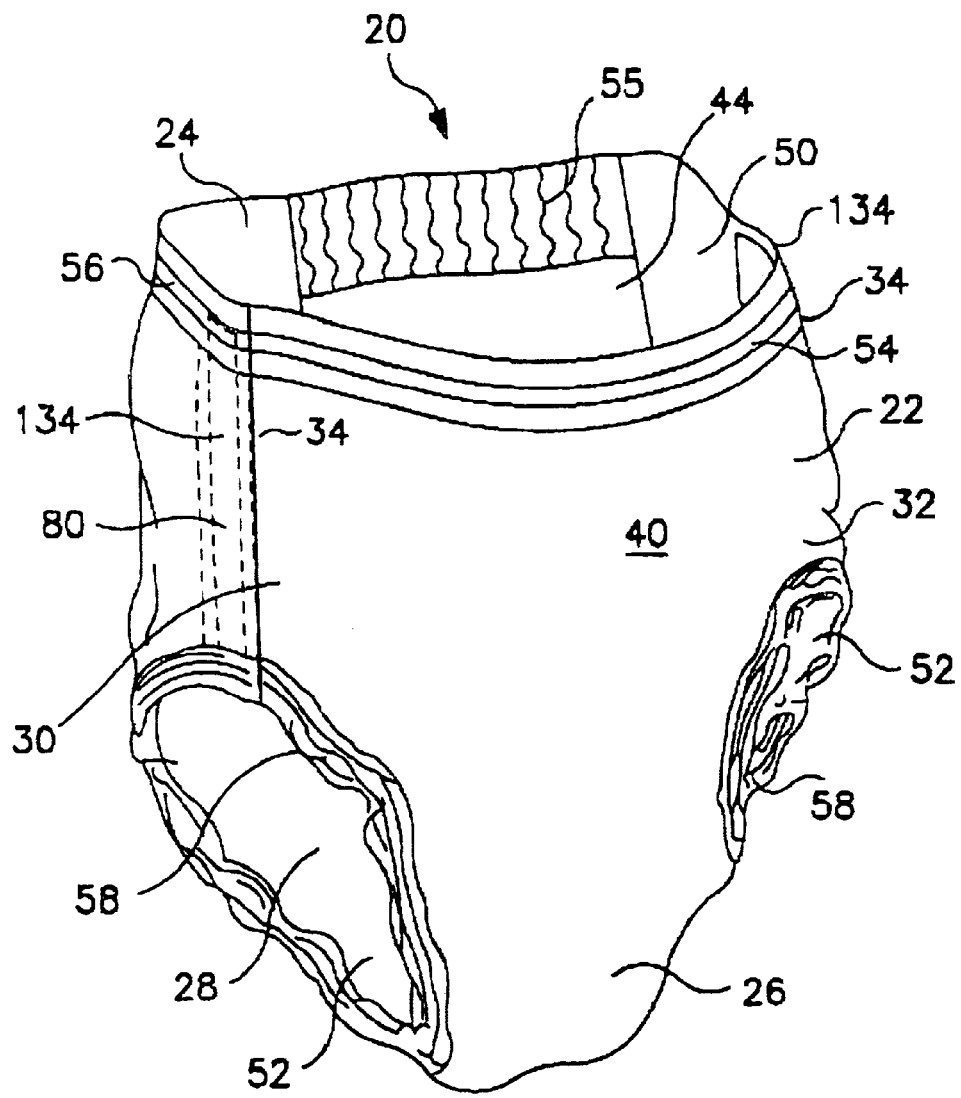
FIG. 1 is a side perspective view of an absorbent garment having an absorbent pad attached to an absorbent chassis, according to one embodiment of this invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to garments or articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover a high percentage, such as about seventy five percent, of its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer or conduct liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable" when used to describe a layer or laminate means that liquid, such as urine, will not pass through the layer or laminate under ordinary use conditions in a direction generally perpendicular to the plane of the layer or laminate at the point of liquid contact.

"Liquid permeable" refers to a layer or laminate that is not liquid impermeable.

Figure 2:
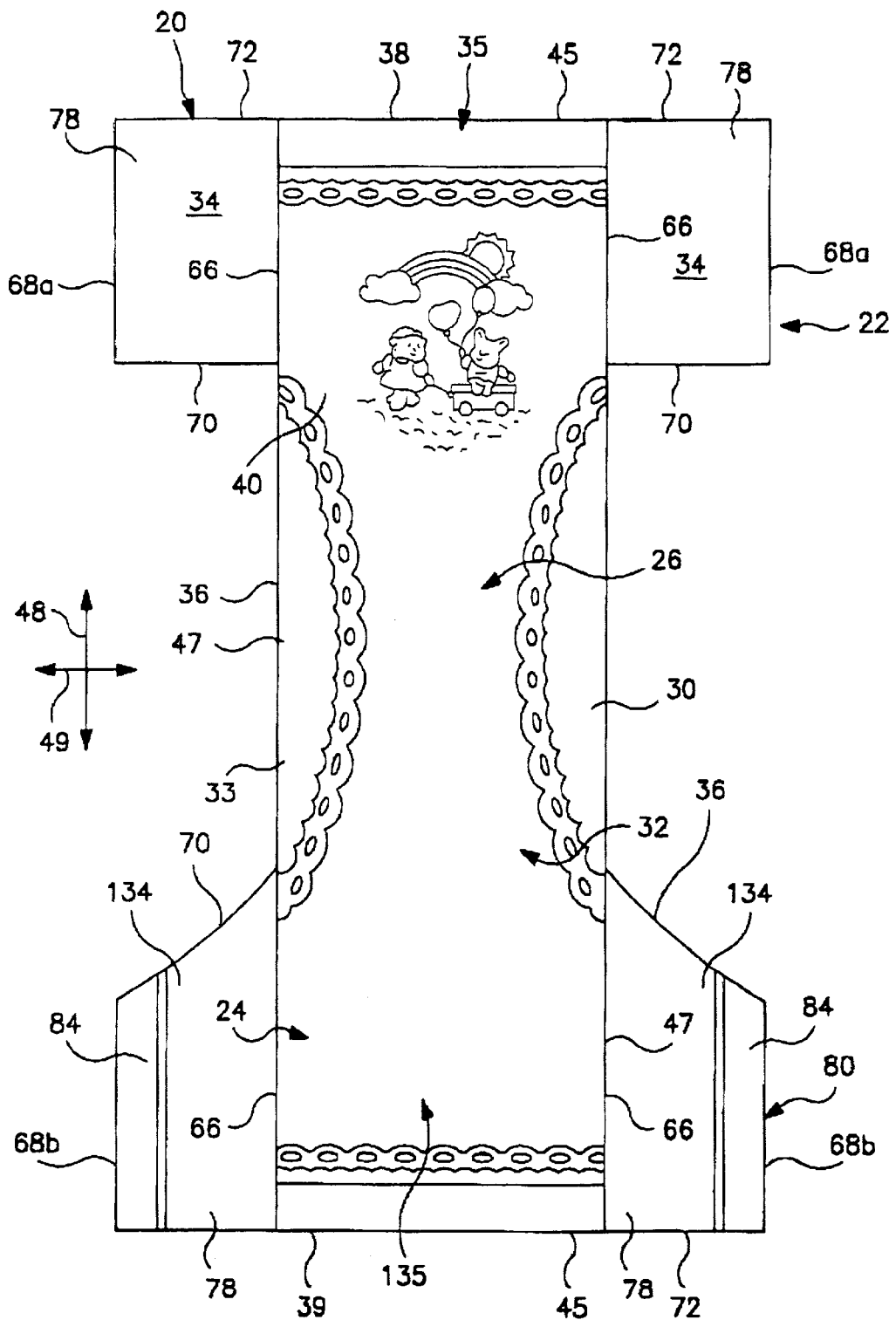
FIG. 2 is a plan view of the absorbent garment of FIG. 1 in a partially disassembled, stretched flat state, and showing the surface of the garment that faces away from the wearer when the garment is worn, according to one embodiment of this invention.
Figure 3:
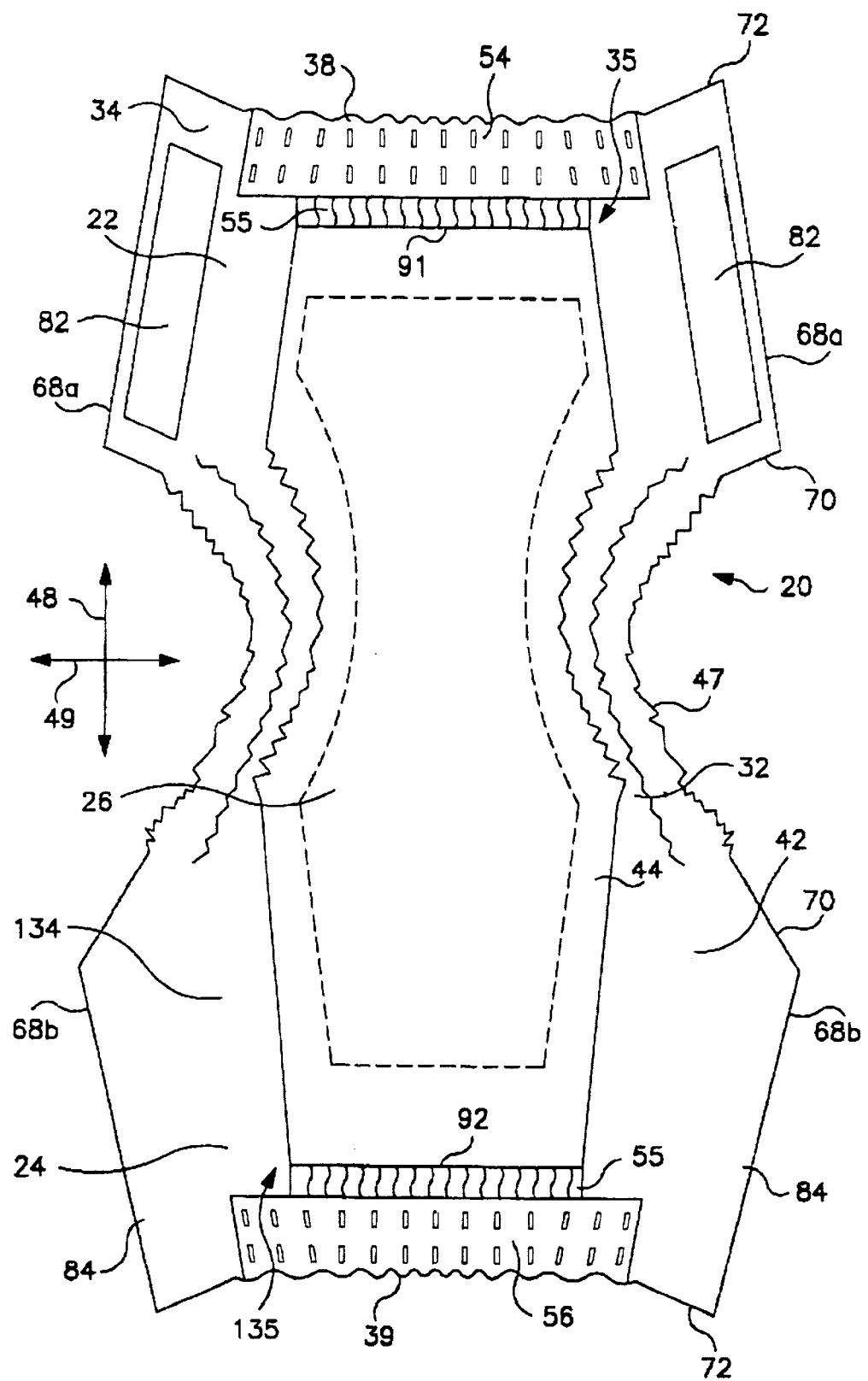
FIG. 3 is a plan view of the absorbent garment of FIGS. 1 and 2 in a partially flat state, and showing the surface of the garment that faces the wearer when the garment is worn, according to one embodiment of this invention.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers can be macrofibers or microfibers that may be continuous or discontinuous. They are generally smaller than about 0.6 denier, but can be greater than about 25 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

A "surface" is formed by the interface between two compositions of matter, one of which may be air, and can include any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE INVENTION

The present invention is directed to a low capacity pant-like absorbent article or garment, for example a training pant 20, having an absorbent pad 44 operatively attached to an absorbent chassis 32 of the training pant 20. In one embodiment of this invention, the absorbent pad 44 is attached to an outer cover 40 at a front waist region 22 and a back waist region 24 of the absorbent chassis 32 using ultrasonic bonds. The low capacity training pant 20 in accordance with this invention is suitable for late-stage toilet training.

The principles of the present invention can be incorporated into any suitable disposable absorbent article. Examples of such suitable articles include diapers, feminine hygiene products, incontinence products, other personal care or health care garments, or the like. For ease of explanation, the description hereafter will be in terms of a child's training pant.

Referring to FIG. 1, a pant-like disposable absorbent article, such as a training pant 20, is illustrated in a fastened condition. The training pant 20 includes an absorbent chassis 32 and a fastening system 80. Suitably, the absorbent chassis 32 has an overall or total initial dry thickness of less than about 3.0 mm, or less than about 2.5 mm, alternatively less than about 2.0 mm. The absorbent chassis 32 defines a front region 22, a back region 24, a crotch region 26 interconnecting the front region 22 and the back region 24, an inner surface 28 which is configured to contact the wearer, and an outer surface 30 opposite the inner surface 28 which is configured to contact the wearer's clothing. As shown in further detail in FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 includes a somewhat rectangular composite structure 33, a pair of transversely opposed front side panels 34, and a pair of transversely opposed back side panels 134. In one embodiment of this invention, the composite structure 33 and side panels 34 and 134 can be integrally formed (FIGS. 1 and 3). Alternatively, the composite structure 33 and the side panels 34 and 134 can include two or more separate elements (FIG. 2). The illustrated composite structure 33 includes an outer cover 40, a bodyside liner 42 which is connected to the outer cover 40 in a superposed relation, and an absorbent pad 44 (FIG. 3) operatively joined to the outer cover 40 and/or the body side liner 42. The composite structure 33 may, in certain embodiments, include a pair of containment flaps (not shown). The somewhat rectangular composite structure 33 has opposite linear end edges 45 that form portions of the front and back waist edges 38 and 39, and opposite linear or curvilinear side edges 47 that form portions of the side edges 36 of the absorbent chassis 32 (FIG. 2). For reference, arrows 48 and 49 depicting the orientation of the longitudinal axis and the transverse axis, respectively, of the training pant 20 are illustrated in FIGS. 2 and 3.

With the training pant 20 in the fastened position as illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the absorbent chassis 32 includes the transversely opposed front side panels 34 and a front center panel 35 (FIG. 2) positioned between and interconnecting the side panels, along with a front waist elastic member or front waistband 54 (FIG. 3) and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member or rear waistband 56 (FIG. 3) and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis 32 or may only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members or bands 58, as are known to those skilled in the art (FIGS. 1 and 3). The waist elastic members 54 and 56 can be operatively joined to the outer cover 40 along the opposite waist edges 38 and 39, and can extend over part or all of the waist edges. In one embodiment of this invention as shown in FIG. 1, the waist elastic members 54 and 56 and the leg elastic members 58 form full waistbands and legbands, respectively.

The leg elastic members 58 are desirably operatively joined to the outer cover 40 and/or the body side liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 54 and 56 and the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer. In one embodiment of this invention, the outer cover material may have bond points and/or perforations.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Desirably, the outer cover 40 is relatively thin and highly breathable. In one embodiment of this invention, the outer cover 40 is a neck-stretched spunbond outer cover 40 having a basis weight of about 1.25 osy. Suitably, the neck-stretched spunbond outer cover 40 has an air permeability of at least about 300 cfm, or at least about 450 cfm, alternatively at least about 550 cfm. Further, the neck-stretched spunbond outer cover 40 has an opacity of less than about 50%, more desirably less than about 45% and still more desirably less than about 42%.

The outer cover 40 according to one embodiment of this invention is stretchable, having a peak load at 20% strain of suitably less than about 100 grams, desirably about 30 grams to about 70 grams. Further, the outer cover 40 can have a hysteresis after 20% strain of about of less than about 60 grams, desirably about 45 grams to about 55 grams.

In one embodiment of this invention, the liquid permeable bodyside liner 42 is connected to the outer cover 40 and is illustrated as overlying the outer cover 40, and may but need not have the same dimensions as the outer cover 40. The bodyside liner 42 may also overlay the absorbent pad 44 so that the absorbent pad 44 is positioned between the outer cover 40 and the bodyside liner 42. The bodyside liner 42 may be sufficiently stretchable so that the absorbent pad 44 can conform to the wearer's body. The bodyside liner 42 is desirably compliant, soft feeling, and non-irritating to the wearer's skin. Further, the bodyside liner 42 can be less hydrophilic than other components of the absorbent chassis 32 to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner 42 can be composed of a meltblown or spunbond web of polyolefin fibers. The bodyside liner 42 can also be a bonded-carded web composed of natural and/or synthetic fibers. The bodyside liner 42 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema Inc., a division of ICI of New Castle, Del., under the trade designation Ahcovel, and from Cognis Corporation of Ambler, Pa., produced in Cincinnati, Ohio, and sold under the trade designation Glucopon 220. The surfactant can be applied by any conventional means, such as spraying, printing, brush coating or the like. The surfactant can be applied to the entire bodyside liner 42 or can be selectively applied to particular sections of the bodyside liner 42, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 can include elastomeric materials, it can be desirable in some embodiments for the composite structure 33 to be generally inelastic, where the outer cover 40 includes materials that are generally not elastomeric.

In one embodiment of this invention, the absorbent pad 44 is positioned overlying the outer cover 40 and the bodyside liner 42 and configured to contact the wearer. Desirably, the absorbent pad 44 is relatively thin, having an initial dry thickness of less than about 2.0 mm, or having an initial dry thickness of less than about 1.5 mm, alternatively having an initial dry thickness of less than about 1.0 mm.

The absorbent pad 44 can be any structure which is generally compressible, conformable, non-irritating to the wearer's skin, and capable of absorbing and retaining liquids and certain body wastes. The absorbent pad 44 can be manufactured in a wide variety of sizes and shapes, and from a wide variety of liquid absorbent materials commonly used in the art. For example, the absorbent pad 44 can suitably include a matrix of hydrophilic fibers, such as a web of cellulosic fluff, mixed with particles of a high-absorbency material commonly known as superabsorbent material. In a particular embodiment, the absorbent pad 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent pad 44 to better contain and absorb body exudates. The concentration of the superabsorbent particles can also vary through the thickness of the absorbent pad 44. Alternatively, the absorbent pad 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material (SAM) is capable of absorbing at least about 15 times its weight in water, and desirably is capable of absorbing more than about 25 times its weight in water. In one embodiment of this invention, the absorbent pad 44 includes a thin, air-laid absorbent material including about 30% SAM, available from EAM Corporation located in Jessup, Ga., U.S.A.

Desirably, the swellable absorbent core 44 is made of a relatively thin, high swelling absorbent material such as an extremely thin, high swelling absorbent composite material sold under the trade name NOVATHIN® available from EAM Corporation located in Jessup, Ga., U.S.A. or an ultra-thin-absorbent (UTA) material including a mixture of SAP and pulp fiber, for example 3.7 g of Favor SXM 9543 SAP, available from Stockhausen GmbH & Co. KG located in Krefeld, Fed. Rep. of Germany, and 3.7 g of NB416 pulp fiber available from Weyerhauser located in Federal Way, Wash., or 2.9 g of Favor SXM 9543 SAP and 6.7 g of NB416 pulp fiber, cut or formed in a roughly 100 mm by 385 mm rectangular pad.

In one embodiment of this invention, the absorbent pad 44 is generally rectangular in shape having a length of about 10 inches to about 16 inches, more desirably about 14 inches to about 15 inches, and a width of about 3 inches to about 5 inches, more desirably about 4 inches. The absorbent pad 44 may have any suitable shape. For example, the absorbent pad 44 may be shaped in the crotch region 26 to have a width of about 2 inches to about 3 inches, more desirably about 2.25 inches to about 2.5 inches.

In one embodiment, the absorbent pad 44 includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent pad 44 in an amount of from about 0 to about 90 weight percent based on total weight of the absorbent pad 44. The absorbent pad 44 suitably has a density within the range of about 0.10 to about 0.50 grams per cubic centimeter. The absorbent pad 44 may or may not be wrapped or encompassed by a suitable tissue wrap that maintains the integrity and/or shape of the absorbent pad 44.

The absorbent pad 44, as shown in FIG. 3, is operatively joined to the outer cover 40 and/or the bodyside liner 42 at the front region 22 and/or the back region 24 of the absorbent chassis 32, desirably using intermittent ultrasonic bonds. The absorbent pad 44 may be joined to the waist regions 22 and/or 24 using any other suitable means, such as adhesives, as is well known in the art. In addition to joining the absorbent pad 44 at the waist regions 22 and 24, the absorbent pad 44 may also be joined to the absorbent chassis 32 in the crotch region 26. For example, the absorbent pad 44 may be bonded or connected to the outer cover 40 and/or the bodyside liner 42 in the crotch region 26 using a one inch square adhesive bond. The absorbent pad 44 may be joined to the outer cover 40 and/or the bodyside liner 42 by other suitable means, as is well known in the art.

Desirably, as shown in FIG. 3, the absorbent pad 44 is permanently joined at a first or front end portion 91 to the front waist region 22 and at a second or rear end portion 92 to the back waist region 24. The absorbent pad 44 can be joined to the waist regions 22 and 24 with a pad attachment 55, wherein the absorbent pad 44 is at least partially suspended between the front region 22 and the back region 24 of the absorbent chassis 32. As used herein the terms "suspended" and "partially suspended" refer to the ability of at least a portion of the absorbent pad 44 to freely hang from and move with respect to the front region 22 and/or the back region 24, for example in a lateral direction, except at the point or region of connection and support. Desirably, the pad attachment 55 is stretchable or extensible in at least one direction, for example in the longitudinal direction 48, so that the absorbent pad 44 can conform to the wearer's body to provide a close or customized fit.

Suitable elastic materials for the pad attachment 55, include but are not limited to, elastic materials such as a stretch-thermal laminate (STL), a neck-bonded laminate (NBL), a reversibly necked laminate, or a stretch-bonded laminate (SBL) material, as described below in reference to the side panels 34 and 134. The pad attachment 55 may also include suitable stretchable but inelastic materials. Alternatively, the pad attachment 55 material may include other woven or nonwoven materials, such as those described above as being suitable for the outer cover 40 or the bodyside liner 42.

Desirably, the training pant 20 has an overall or total absorbent capacity not greater than about three times an anticipated insult volume, more desirably not greater than about two times the anticipated insult volume, and a high saturated capacity, making the absorbent pad 44 a very efficient absorbent structure. In one embodiment of this invention, a single void training pant 20 for children between about 18 months and about 48 months old, generally accommodates insult volumes of less than about 300 grams (g), suitably about 60 g to about 200 g, desirably about 100 g to about 150 g. In alternative embodiments, the training pant 20 may accommodate greater insult volumes, if desired.

The overall absorbent capacity of the absorbent core 44 is expressed in terms of grams (g) of fluid absorbed (and retained). The overall absorbent capacity of the absorbent core 44 can, in particular embodiments, be less than about 300 g, suitably about 60 g to about 200 g, desirably about 100 g to about 160 g, and alternatively about 140 g to about 150 g. The saturated capacity (i.e. absorbent efficiency) of the absorbent core 44 is expressed in terms of grams (g) of fluid retained/gram (g) of absorbent structure, wherein a higher value represents a greater efficiency. Desirably, the saturated capacity of the absorbent core 44 is greater than about 7 g/g, more desirably about 9 g/g to about 11 g/g, and still more desirably greater than about 12.0 g/g. Both overall absorbent capacity and saturated capacity of the absorbent pad 44 are determined by a modified saturated capacity test, discussed below.

For example, an absorbent pad 44 comprising a fluff pulp and superabsorbent material, as well as other components, is able to retain a specific amount of fluid that is determined by the individual fluid capacities of the components and their relative percentages within the absorbent structure 44. The superabsorbent material (SAM) is highly efficient, whereas the fluff pulp material is moderately efficient. Further, some synthetic fibers such as polyester fibers are generally inefficient. An "efficient" absorbent structure will retain a relatively large volume of fluid, whereas an "inefficient" absorbent structure will retain a relatively small volume of fluid.

The absorbent chassis 32 can also incorporate other materials that are designed primarily to receive, temporarily store, and/or transport liquid along the mutually facing surface with the absorbent pad 44, thereby maximizing the overall absorbent capacity of the absorbent pad 44, if desired. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24, and may be releasably attached to one another by a fastening system 80. More particularly, as shown best in FIG. 2, the front side panels 34 can be permanently bonded to and extend transversely beyond the side edges 47 of the composite structure 33 in the front region 22 along attachment lines 66, and the back side panels 134 can be permanently bonded to and extend transversely beyond the linear side edges of the composite structure in the back region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68b of the back panel 134, as is best shown in FIG. 2.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 2, the interior portions 78 are disposed between the distal edges 68a, 68b and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola;

and 5,046,272 issued Sep. 10, 1991 to Vogt et al.; all of which are incorporated herein by reference. In particular embodiments, the elastic material includes a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al., all of which are incorporated herein by reference. Alternatively, the side panel material may include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). The fastening system 80 may permanently fasten side panels 34 and 134 to form the training pant 20. More desirably, referring to FIGS. 2 and 3, the fastening system 80 includes fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

The absorbent chassis 32 and the fastening system 80 together define a refastenable product having a waist opening 50 and a pair of leg openings 52. When the fastening system is engaged, the refastenable product includes a pair of front side panels 34 extending from the waist opening 50 to each leg opening 52, a pair of back side panels 134 extending from the waist opening 50 to each leg opening 52, an elastomeric front waistband 54 disposed on the front side 22 and positioned between the pair of elastomeric front side panels 34, an elastomeric back waistband 56 disposed on the back side 24 and positioned between the pair of back side panels 134, and at least a pair of the leg elastic members 58 which partially encircle each leg opening 52. More preferably, more than one leg elastic member 58 partially or fully encircles each leg opening 52. Each leg elastic member 58 extends from adjacent front side panel 34 on the front side 22 to adjacent back side panel 134 on the back side 24.

As described herein, the various components of the absorbent garment 20 can be integrally assembled together employing various types of suitable attachment means, such as adhesive, sonic and thermal bonds or combinations thereof.

The resulting product is a low capacity training pant 20 having an absorbent pad 44 suspended between the front waist region 22 and the back waist region 24 of the absorbent chassis 32.

EXAMPLES

A neck-stretched spunbond outer cover (CODE 1) made in accordance with one embodiment of this invention, was tested and compared with outer cover and side panel materials of commercial products. Additionally, the overall capacity and the saturated capacity of the absorbent structures contained in commercially available products (CODE 2 through CODE 7) were determined using a Modified Saturated Capacity Test. The test results are displayed in Table 1, below.

Tests to determine and compare the air permeability, the opacity and the stretch characteristics of the neck-stretched laminate outer cover of the invention with the outer cover and side panel materials of commercially available products included the Air Permeability Test, the ISO Opacity Test and the Cycle Test, each described below.

The commercial products tested include the following products, designated CODE 2 through CODE 9.

CODE 2 was a DEPEND® Disposable Protective Underwear (size small/medium) manufactured by Kimberly-Clark Corporation, Neenah, Wis., U.S.A., and purchased in the United States in June 2001.

CODE 3 was a BELT-FREE Disposable Undergarment (size large) purchased from Walgreen's Drug Store, Neenah, Wis., U.S.A., in June 2001.

CODE 4 was a Disposable Protective Underwear (size small/medium) purchased from Walgreen's Drug Store, Neenah, Wis., U.S.A., in June 2001.

CODE 5 was a KOTEX® Personals® Disposable Protective Panty (size 8/9/10) representative of products manufactured by Kimberly-Clark Corporation, Neenah, Wis., U.S.A.

CODE 6 was a MERRIES TOREPANTS® training pant (size large) manufactured by Kao Corporation, Japan, and purchased in 2000.

CODE 7 was a MERRIES SLENDER FIT® pant diaper (size large) manufactured by Kao Corporation, Japan, and purchased in 2000.

CODE 8 was a pink spunbond laminate (SBL) side panel, which Kimberly-Clark Corporation uses in its manufacture of PULL-UPS® training pants.

CODE 9 was a blue spunbond laminate (SBL) side panel, which Kimberly-Clark Corporation uses in its manufacture of PULL-UPS® training pants.

obtained with different size test heads are not always comparable, samples to be compared should be tested with the same size test head.

The NULL RESET button is pressed prior to every series of tests, or when the red light is displayed. The test head must be open (no specimen in place) and the vacuum pump must be at a complete stop before the NULL RESET button is pressed.

The following procedure was followed to test the Air Permeability of each test material:

TABLE 1

TEST RESULTS

| Code | Air Permeability (cfm) | ISO Opacity (%) | Tensile Strength: Peak Load at 20% Strain, in g of force (avg.; high/low) | Recovery: % Hysteresis after 20% Strain (avg.; high/low) | Overall Capacity of Absorbent (g saline) | Saturated Capacity of Absorbent (g saline/g absorbent) |
|---|---|---|---|---|---|---|
| 1 | 587 | 41 | 53.7; 67.1/37.0 | 52.3; 54.0/49.0 | N/A | N/A |
| 2 | 230 | 53* | 6713; 9559/4063 | 70.9;72.3/69.5 | 480 | 13 |
| 3 | 546 | 43* | 6552; >10,000/2859** | 67.5; 68.7/64.6*** | 750 | 14.6 |
| 4 | 283 | 42* | 4020; 5787/2303 | 69.5; 70.3/68.6 | 437 | 11.7 |
| 5 | 656 | 52 | 5758; 771/3925 | 67.8; 69.0/66.9 | 223 | 4.2 |
| 6 | 870 | 43 | 4091; 6474/2114 | 81.6; 82.2/80.9 | 239 | 12.2 |
| 7 | 902 | 42 | 3653; 6183/1849 | 80.3; 81.8/72.1 | 506 | 15.1 |
| 8 | 452 | 65 | 175; 194/148 | 20.8; 22.0/19.6 | **** | **** |
| 9 | 502 | 91 | 153; 168/135 | 21.6; 22.8/20.7 | **** | **** |

*Two test samples were placed together for opacity test.
**Three samples exceeded the load cell limit of about 10,000 g, and were approximated with 10,000 g force; therefore, the average value is a lower limit.
***The average is of only seven samples due to excessive loads exerted by the three samples that prevented completion of those specimen trials.
****The overall capacity of Pull-Ups ® Training Pants, size sm/med for boys, is about 420 g; the saturated capacity is about 17.8 g/g.

Test Methods

Air Permeability Test

The Air Permeability of the test materials was tested using a Textest FX 3300 apparatus, available from Schmid Corporation, Spartanburg, S.C., U.S.A.

The nonwoven material test samples were clean and free of defects. The sample areas to be analyzed were also free from printing or perforation lines. The sample specimens were cut into square shapes approximately 2.25 inches (5.7 cm) on each side. Ten individual specimens were analyzed, and the results were averaged.

Each specimen was cut and placed so that the specimen extended beyond the clamping area. The test specimens were obtained from areas of the sample that were free of folds, crimp lines, perforations, wrinkles, and/or any distortions that make them abnormal from the rest of the test material.

The tests were conducted in a standard laboratory atmosphere of 23±1° C. (73.4±1.8° F.) and 50±2% humidity. The instrument is turned on and allowed to warm up for at least 5 minutes before testing any samples. The instrument is calibrated based on the manufacturer's guidelines before the test material is analyzed. The rubber plate or cover is removed and the NULL RESET button is pressed to reset pressure sensors to zero. Before testing, and if necessary between samples or specimens, the dust filter screen can be cleaned, following the manufacturer's instructions. The following specifications are selected for data collection: (a) Unit of measure: cubic feet per minute (cfm); (b) test pressure: 250 Pascal (Pa; water column 1 inch/2.54 cm); and (c) test head: 5 square centimeters ($cm^2$). Since test results 1. Place the specimen over the lower test head.
2. Start the test by manually pressing down on the clamping lever until the vacuum pump automatically starts.
3. Stabilize the Range Indicator light in the green or yellow area using the RANGE knob. The measuring range may be changed while the vacuum pump is running only for testing apparatuses built in 1992 or later.
4. After the digital display stabilizes, the air permeability of the specimen will be displayed in the desired unit of measure. Record the value. Press down on the clamping lever to release the specimen.
5. Repeat the procedure for all specimens.
6. In the case of bulky specimens that may permit lateral air flow of significant magnitude, each specimen should be tested twice. Prior to the second test, the specimen should be covered with the rubber plate provided by the manufacturer. The rubber plate will be located between the specimen and the upper test head. The plate should be left in place for the second test. The air permeability of the material is calculated as the difference in the results between the two tests.
7. When testing is complete, cover the lower test head with the supplied rubber plate.
8. Calculate an average air permeability value from the permeabilities of the 10 individual specimens. A standard deviation can also be calculated if desired.

ISO Opacity Test

The Opacity of the test materials was tested using a Technibrite Micro TB-1C apparatus, available from Technidyne Corporation, New Albany, Ind., U.S.A.

The nonwoven test material samples were clean and free of defects. The testing areas to be analyzed are free from printing and/or perforation lines. The samples were cut into square shapes approximately 2.25 inches (5.7 cm) on each side. At least ten specimens were tested individually and stacks of 25 specimens each were used for "infinite stacks" to provide a full opacity. Each infinite stack is used as a control for each of five different individual specimens. If 25 specimen sheets per infinite stack are insufficient to ensure that no noticeable change in readings results when additional sheets are added, the number of specimen sheets in each infinite stack should be increased until this condition is satisfied.

The tests were conducted in a standard laboratory atmosphere of 23±1° C. (73.4±1.8° F.) and 50±2% relative humidity. A black body cup must be on the sample holder for all single-sheet opacity readings. A Y (green) filter is in the active position. The infinite stacks and individual specimens remain in order; i.e., stack 1 with specimens 1–5; stack 2 with specimens 6–10; etc.

The instrument is turned on and allowed to warm up for at least 30 minutes before testing any samples. The instrument is calibrated as directed in the instrument manufacturer's instruction manual. The calibration is verified at least once per day, prior to testing. The swing-in standard should be kept clean and free of fingerprints, using lint-free wipes or lens paper and a lens cleaner that does not leave a residue, as needed.

The samples are compared employing the ISO opacity readings that reflect an average value for at least 10 individual specimens of each sample.

The following procedure was followed to test the Opacity of each test material:

1. Press the REPROGRAM button and select ISO OPACITY for data output.
2. Press PRINT to complete the routine and check the selected output type for correctness.
3. Press the QC button, enter the sample number, and press PRINT again.
4. Load stack 1 onto the spring-loaded sample holder. Release the spring-loaded sample holder, with the stack, so it is tight against the port.
5. Press SCAN.
6. Remove the stack.
7. Place individual sample 1 onto the spring-loaded sample holder. Press PRINT.
8. Repeat steps 4–7 with successive specimens until individual specimens 1–5 have each been tested.
9. Repeat steps 2–8 for stack 2 and specimens 6–10; these steps can be repeated as many times as needed until all individual specimens have been tested against their respective stacks. Keep individual samples and sets in order.
10. Average the individual "Calculated TAPPI opacity" values from the full set of tests.

Material Elasticity

Cycle Test Procedure

This procedure is a single-cycle tension bench test to measure the degree of extensibility of a test material. The procedure measures load values when the material is placed under a particular amount of strain (percent extension). Load values are determined on both extension and retraction phases of the test. A test material is cycled to a specific elongation/extension rather than to a specific load value. This test method can generate the following data: (a) load values as the material is being cycled from 0 to 20% extension (% strain); (b) load values as the material is being cycled back from 20 to 0% of original extension; and (c) peak load at 20% extension.

A material sample is placed between clamps on a tensile tester. The width of the material to be tested is 2¼ inches (57 mm). The gage length is 1 inch (25 mm) between the ends of the clamp faces. The term "load" refers to the gram value measured by the load cells in the tensile tester.

The jaws are separated until a load of a specific level is detected in the load cell. This pre-load removes any slack in the material. At this time, the load is re-zeroed and the jaws continue to separate to provide an increase in gage length of 20% beyond the pre-load gage distance, which equates to a percent extension or percent strain in the material of 20%. The load values generated on the material throughout this process are recorded. The jaws are then brought back together to the original gage length, and load values are again recorded during the retraction. If slippage of specimens between the jaws occurs during testing, the grip faces of the jaws can be adapted to increase friction with specimens.

The standard test is one cycle per specimen. The percent hysteresis of a specimen may be calculated by the software using values from both extension and retraction curves.

Suitable materials include nonwoven webs such as spunbonded thermoplastic polymers. In materials possessing significant extensibility or elastomeric nature in a particular dimension, this dimension should be analyzed by this method. Additionally, where possible, it may be desirable to test material specimens along the direction in which the sample was originally manufactured, if from a continuous web. However, this direction may not always be determinable.

Some materials may exhibit anisotropy (differing properties when measured in different directions) as a result of being manufactured as continuous webs, or as a result of other aspects of the manufacturing process. Alignment of fibers in nonwoven materials, as well as other treatments such as necking or creping, may result in load values in one direction that are dissimilar from load values in other directions. For materials that are obtained from commercial products, it may not be immediately apparent which dimension will provide higher or lower load values; in addition, the direction in which a material was manufactured may not be determinable. For the above reasons, an average of at least ten specimens should be calculated for each sample, and high and low values contributing to the average should also be reported.

The apparatus used includes: (a) a Constant Rate of Extension (CRE) tensile tester, such as a MTS tensile tester model Synergie 200 Test Bed, available from MTS® Systems Corporation, Research Triangle Park, N.C., U.S.A.; (b) a suitable cell selected so the majority of the peak load values fall between the manufacturer's recommended ranges of load cell's full scale value, such as a Model 100N load cell, available from MTS® Systems Corporation, Research Triangle Park, N.C., U.S.A.; (c) Operating software and data acquisition system, such as MTS TestWorks® for Windows software version 4, available from MTS® Systems Corporation, Research Triangle Park, N.C., U.S.A.; and (d) pneumatic-action grips, top and bottom, suitable grips include grips identified as part number 2712–003 available from Instron Corporation, Canton, Mass., U.S.A., wherein the grip faces are about 25 mm by about 75 (1 inch by 3 inches).

The tests were conducted in standard ASTM laboratory conditions. A material specimen at least about 2 inches (51 mm) in length (the direction of tensile testing) and exactly 2.25 inches (57 mm) in width (perpendicular to testing) can be used. At least ten specimens of each sample should be tested, and the results averaged.

Tensile Tester test conditions

Break sensitivity: 90%
Break threshold: 0.5 pounds of force
Data acquisition rate: 100 Hz
Preload: Yes
Preload: 5 grams
Preload crosshead speed: 6.350 mm/min
Hold time 1: 0 sec
Hold time 2: 0 sec
Slowdown extension: 0 mm
Strain 1 endpoint: 20% (of gage length following preload)
Strain 2 endpoint: 0% (of original gage length)
Test speed: 12.7 mm/min
Zero extension after preload: Yes
Full scale load: 10,000 g
Gage length: 0.1 inch (25 mm)
Number of cycles: 1

The following procedure was followed to test the Elasticity of each test material:

A. Calibrate the load cell using the Testworks software, at the beginning of each work session.
B. Using the tensile frame pushbutton controls for crosshead position, move grips to provide a gage length of 1 inch (25 mm). Calibrate the software to this initial gage length.
C. Place a material specimen so that it is centered between the grips, held in a centered position within each grip, and oriented correctly (2¼ inch/57 mm dimension running the width direction on the grips). The specimen's vertical edges should be perpendicular to the grip faces.
D. Close the grips on the specimen, holding the specimen in such a way as to minimize slack in the specimen, but do not place the specimen under tension. Ensure that the load at this point is less than 5 grams. If the load is greater than five grams, release the lower grip and zero the load cell. Close the lower grip, again ensuring that the specimen is neither under tension nor buckled with excessive slack. Continue checking the starting load and following the above procedure until the starting load is under 5 grams.
E. Run the single cycle test using the above parameters by clicking on the RUN button.
F. When the test is complete, save the data to a sample file.
G. Remove the specimen from the grips.
H. Run additional specimens of a given sample using steps C-E and G; the data for all specimens should be saved to a single file.
I. Continue testing all samples in this manner.
J. Report data for each sample in the following way:
   Average peak load @ 20% strain
   Highest individual peak load @ 20% strain
   Lowest individual peak load @ 20% strain A specimen with a peak load that exceeds the limits of the load cell (~10,000 g) should have a peak load listed as >10,000 g. The average calculation for that sample should use 10,000 g as the peak load for that specimen, with a notation made that the average is conservative (low) due to rounding down at least one peak load level to 10,000 g. The highest individual peak load for that sample would be listed as >10,000 g.

Modified Saturated Capacity Test

Figure 4:
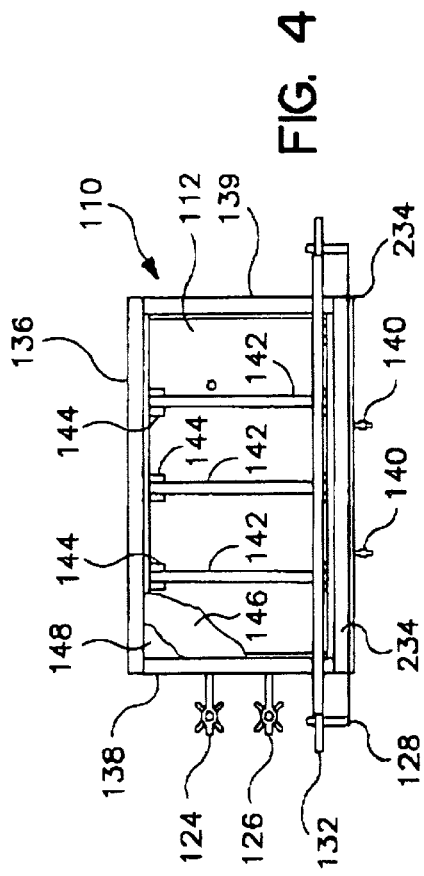
FIG. 4 representatively shows a partially cut away top view of a saturated capacity tester.
Figure 6:
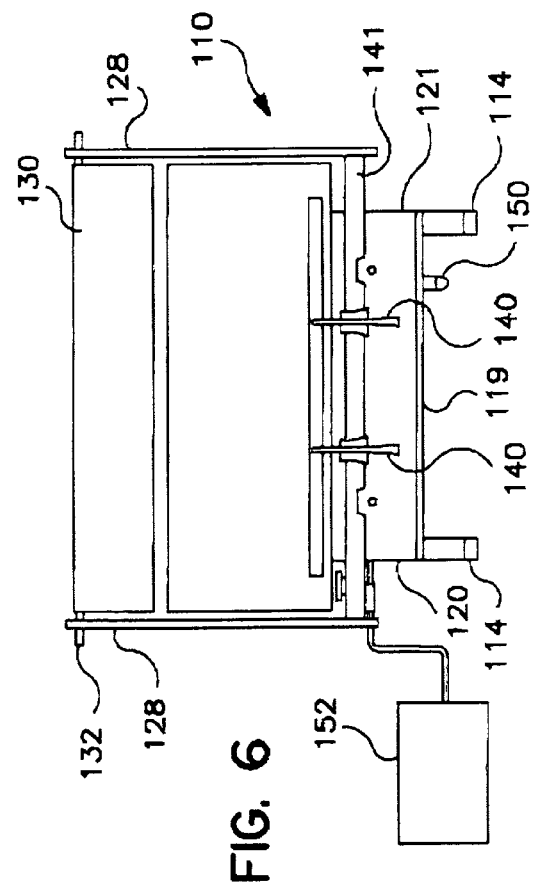
FIG. 6 representatively shows a rear view of a saturated capacity tester.
Figure 5:
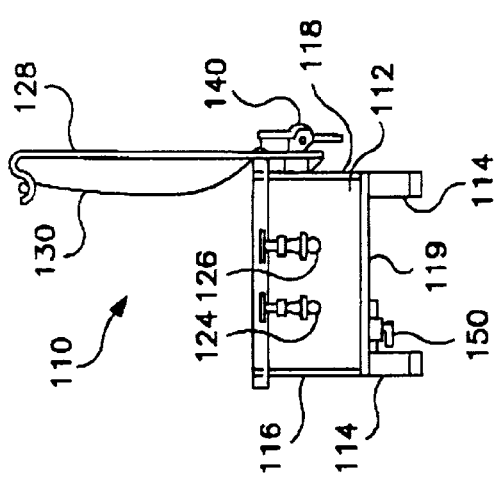
FIG. 5 representatively shows a side view of a saturated capacity tester.

Saturated Capacity is determined using a Saturated Capacity (SAT CAP) tester with a Magnahelic vacuum gage and a latex dam. Referring to FIGS. 4–6, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex sheet 130 is looped around a dowel member 132 to facilitate grasping and to allow a convenient movement and positioning of the latex sheet 130. In the illustrated position, the dowel member 132 is shown supported in a hanger assembly 128 to position the latex sheet 130 in an open position away from the top of the vacuum chamber 112.

A bottom edge of the latex sheet 130 is clamped against a rear edge support member 234 with suitable securing means, such as toggle clamps 140. The toggle clamps are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 234, the apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inches.

A layer of egg crating type material 146 is positioned on top of the support shafts 142 and the top edges of the wall members of the vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 0.19 mesh nylon screening 148, which measures 23.5 inches by 14 inches, is placed on top of egg crating material 146.

A suitable drain line and a drain valve 150 connect to bottom plate member 119 of the vacuum chamber 112 to provide a convenient mechanism for draining liquids from the vacuum chamber 112. The various wall members and support members of tester apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0–100 inches of water, such as a No. 2100 gauge available from Dwyer Instrument Incorporated.

The dry product or other absorbent structure is weighed and then placed in excess 0.9% saline solution and allowed to soak for 20 minutes. After the 20 minute soak time, the absorbent structure is placed on the egg crate material and mesh nylon screening of the Saturated Capacity tester. The latex sheet is placed over the absorbent structure(s) and the entire egg crate grid so that the latex sheet creates a seal when a vacuum is drawn on the tester. A vacuum of 0.5 pounds per square inch (psi) is held in the Saturated Capacity tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight.

The Overall Capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula:

SAT CAP=(wet weight−dry weight)/dry weight;

wherein the SAT CAP value has units of grams fluid/gram absorbent. For both Overall Capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example Hi-Dri® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A low capacity disposable absorbent article comprising:
   an outer cover defining a front region, a back region and a crotch region interconnecting the front region and the back region; and
   a first front side panel of the front region permanently connected to a corresponding first back side panel of the back region;
   a second front side panel of the front region permanently connected to a corresponding second back side panel of the back region;
   an absorbent pad joined at a first end portion to the front region and joined at a second end portion to the back region, wherein the absorbent pad is at least partially suspended between the front region and the back region, the absorbent pad having an overall absorbent capacity of less than 300 grams.

2. The absorbent article of claim 1 further comprising a stretchable pad attachment operatively joining the front region and the absorbent pad.

3. The absorbent article of claim 1 further comprising a stretchable pad attachment operatively joining the back region and the absorbent pad.

4. The absorbent article of claim 1 wherein the outer cover comprises a single-piece outer cover.

5. The absorbent article of claim 1 wherein the outer cover comprises a neck-stretched spunbond material.

6. The absorbent article of claim 1 wherein the outer cover is breathable.

7. The absorbent article of claim 1 wherein the outer cover has an air permeability of at least about 300 cfm.

8. The absorbent article of claim 1 wherein the outer cover has an air permeability of at least about 450 cfm.

9. The absorbent article of claim 1 wherein the outer cover has an air permeability of at least about 550 cfm.

10. The absorbent article of claim 1 wherein the outer cover has an opacity of less than about 50%.

11. The absorbent article of claim 1 wherein the outer cover has an opacity of less than about 45%.

12. The absorbent article of claim 1 wherein the outer cover has an opacity of less than about 42%.

13. The absorbent article of claim 1 wherein the absorbent pad comprises an absorbent having at least about 30% super absorbent material.

14. The absorbent article of claim 1 wherein the absorbent pad has an overall absorbent capacity of about 60 grams to about 200 grams.

15. The absorbent article of claim 1 wherein the absorbent pad has an overall absorbent capacity of about 100 grams to about 160 grams.

16. The absorbent article of claim 1 wherein the absorbent pad has an overall absorbent capacity of about 140 grams to about 150 grams.

17. The absorbent article of claim 1 wherein the absorbent pad has a saturated capacity greater than about 7 g/g.

18. The absorbent article of claim 1 wherein the absorbent pad has a saturated capacity of about 9 g/g to about 11 g/g.

19. The absorbent article of claim 1 wherein the absorbent pad has a saturated capacity greater than about 12.0 g/g.

20. The absorbent article of claim 1 wherein the absorbent pad is bonded to the outer cover in the crotch region.

21. The absorbent article of claim 1 wherein the absorbent pad has a width in the crotch region of about 2.0 inches to bout 3.0 inches.

22. An absorbent garment comprising:

an absorbent chassis having an outer cover;

a first front side panel bonded to a front region of the outer cover and permanently connected to a corresponding first back side panel bonded to a back region of the outer cover;

a second front side panel bonded to the front region and permanently connected to a corresponding second back side anel bonded to the back region;

an absorbent pad suspended between a first region of the outer cover and a second region of the outer cover, the absorbent pad having an overall absorbent capacity of less than 300 grams;

a first stretchable pad attachment connected at a first end portion to the first region and at a second end portion to the absorbent pad; and a second stretchable pad attachment connected at a first end portion to the second region and at a second end portion to the absorbent pad.

23. The absorbent garment of claim 22 wherein the first stretchable pad attachment and the second stretchable pad attachment each is stretchable in at least a longitudinal direction of the absorbent chassis.

24. The absorbent garment of claim 22 wherein the absorbent garment has an initial dry thickness less than about 3.0 mm.

25. The absorbent garment of claim 22 wherein the absorbent garment has an initial dry thickness less than about 2.5 mm.

26. The absorbent garment of claim 22 wherein the absorbent garment has an initial dry thickness less than about 2.0 mm.

27. The absorbent garment of claim 22 wherein the absorbent pad has an initial dry thickness less than about 2.0 mm.

28. The absorbent garment of claim 22 wherein the absorbent pad has an initial dry thickness less than about 1.5 mm.

29. The absorbent garment of claim 22 wherein the absorbent pad has an initial dry thickness less than about 1.0 mm.

30. The absorbent garment of claim 22 wherein the absorbent pad has an initial dry thickness of about 0.5 mm to about 1.0 mm.

31. The absorbent garment of claim 22 comprising a single insult training pant.

32. The absorbent garment of claim 22 comprising a diaper.

33. The absorbent garment of claim 22 comprising child training pants.

34. The absorbent garment of claim 22 comprising an adult incontinence garment.

35. An absorbent garment comprising:

an absorbent chassis comprising a front region and a back region, and defining a waist opening, a first leg opening and a second leg opening;

a first front side panel bonded to the front region and permanently connected to a corresponding first back side panel bonded to the back region to form the first leg opening:

a second front side panel bonded to the front region and permanently connected to a corresponding second back side panel bonded to the back region to form the second leg opening;

an absorbent pad suspended between the front region and the back region, the absorbent pad having an overall absorbent capacity of less than 300 grams;

a first stretchable pad attachment connected at a first end portion to the front region and at a second end portion to the absorbent pad; and a second stretchable pad attachment connected at a first end portion to the back region and at a second end portion to the absorbent pad.

36. The absorbent garment of claim 35 wherein the first stretchable pad attachment is connected at the first end portion to a front waist elastic member.

37. The absorbent garment of claim 35 wherein the second stretchable pad attachment is connected at the first end portion to a rear waist elastic member.

* * * * *